(12) United States Patent
Shing et al.

(10) Patent No.: US 12,409,450 B2
(45) Date of Patent: Sep. 9, 2025

(54) BIOSENSING TEST STRIP AND BIOSENSING TEST METHOD

(71) Applicant: APEX BIOTECHNOLOGY CORPORATION, Hsinchu (TW)

(72) Inventors: Chung-Yen Shing, Keelung (TW); Bo-Chun Lin, Su-Ao Township (TW); Sz-Hau Chen, Taipei (TW); Hong-Wen Chen, Taichung (TW); Heng-Chia Liang, Minxiong Township (TW)

(73) Assignee: APEX BIOTECHNOLOGY CORP., Hsinchu (TW)

( * ) Notice: Subject to any disclaimer, the term of this patent is extended or adjusted under 35 U.S.C. 154(b) by 679 days.

(21) Appl. No.: 17/771,467

(22) PCT Filed: Nov. 12, 2020

(86) PCT No.: PCT/CN2020/128387
§ 371 (c)(1),
(2) Date: Apr. 23, 2022

(87) PCT Pub. No.: WO2021/093812
PCT Pub. Date: May 20, 2021

(65) Prior Publication Data
US 2022/0379308 A1 Dec. 1, 2022

Related U.S. Application Data

(60) Provisional application No. 62/935,473, filed on Nov. 14, 2019.

(51) Int. Cl.
*B01L 3/00* (2006.01)
*G01N 27/327* (2006.01)

(52) U.S. Cl.
CPC .... *B01L 3/502715* (2013.01); *G01N 27/3272* (2013.01); *B01L 2200/16* (2013.01);
(Continued)

(58) Field of Classification Search
CPC ........... B01L 3/502715; B01L 2200/16; B01L 2300/0645; B01L 2300/069;
(Continued)

(56) References Cited

U.S. PATENT DOCUMENTS 8,252,248 B2 * 8/2012 Kramer ............ B01L 3/502715
435/287.8
2004/0109793 A1 6/2004 McNeely et al.
(Continued)

FOREIGN PATENT DOCUMENTS

CN 101178373 5/2008
CN 108020584 5/2018
(Continued)

OTHER PUBLICATIONS

First Examination Report for counterpart IN Application No. 202247028921 dated Jul. 13, 2022.
(Continued)

*Primary Examiner* — Jennifer Wecker
*Assistant Examiner* — Britney N. Washington
(74) *Attorney, Agent, or Firm* — LIU & LIU

(57) ABSTRACT

Disclosed are a biosensing test strip (100, 200, 300, 500, 600, 700, 800, 900, 1000, 1100) and a biosensing test method. The biosensing test strip (100, 200, 300, 400, 500, 600, 700, 800, 900, 1000, 1100) comprises: a reaction layer (120, 220, 720, 820) provided with a reaction flow channel (121, 221, 821, 920, 1020); a partition plate layer (130, 230) located above the reaction layer (120, 220, 720, 820) and covering the reaction flow channel (121, 221, 821, 920, 1020); an exhaust layer (140, 240, 540, 640) located above the partition plate layer (130, 230), with the exhaust layer (140, 240, 540, 640) being provided with an exhaust flow channel (141, 241, 550, 650); and a communication hole passing through the partition plate layer (130, 230) to enable (Continued)

the exhaust flow channel (141, 241, 550, 650) to be in communication with the reaction flow channel (121, 221, 821, 920, 1020).

10 Claims, 14 Drawing Sheets

(52) U.S. Cl.
CPC . *B01L 2300/0645* (2013.01); *B01L 2300/069* (2013.01); *B01L 2300/0816* (2013.01); *B01L 2300/0883* (2013.01); *B01L 2300/0887* (2013.01); *B01L 2400/0688* (2013.01); *B01L 2400/0694* (2013.01)

(58) Field of Classification Search
CPC ..... B01L 2300/0816; B01L 2300/0883; B01L 2300/0887; B01L 2400/0688; B01L 2400/0694; B01L 3/502723; B01L 3/502746; G01N 27/3272; G01N 33/483
See application file for complete search history.

(56) References Cited

U.S. PATENT DOCUMENTS

| | | | | |
|---|---|---|---|---|
| 2004/0206408 | A1* | 10/2004 | Peters | F16K 99/0028 |
| | | | | 137/825 |
| 2006/0078986 | A1 | 4/2006 | Ly et al. | |
| 2008/0031778 | A1 | 2/2008 | Kramer | |
| 2008/0110768 | A1* | 5/2008 | Bae | G01N 27/3272 |
| | | | | 205/777.5 |
| 2013/0280725 | A1 | 10/2013 | Ismagilov et al. | |
| 2013/0309679 | A1 | 11/2013 | Ismagilov et al. | |
| 2017/0219576 | A1 | 8/2017 | Heavner | |
| 2018/0125400 | A1* | 5/2018 | Yang | A61B 5/14532 |
| 2018/0164243 | A1* | 6/2018 | Noumi | A61B 5/14532 |
| 2019/0178787 | A1* | 6/2019 | Anderson | G01F 23/02 |

FOREIGN PATENT DOCUMENTS

| | | |
|---|---|---|
| CN | 109759156 | 5/2019 |
| JP | 2008-505330 | 2/2008 |
| JP | 2015-514997 | 5/2015 |
| JP | 2017-3585 | 1/2017 |
| JP | 2019-509498 | 4/2019 |
| TW | M572990 U | 1/2019 |
| WO | 2009/024916 | 2/2009 |
| WO | 2011071772 | 6/2011 |
| WO | 2020060475 | 3/2020 |

OTHER PUBLICATIONS

Search Report dated Dec. 21, 2023 issued in counterpart SG Application No. 11202204454U.
Written Opinion dated Dec. 23, 2023 issued in counterpart SG Application No. 11202204454U.
Office Action dated Apr. 3, 2023 issued in counterpart EP Application No. 20 000 408.3.
Office Action dated Apr. 18, 2023 issued in counterpart JP Application No. 2022-526431.
Office Action dated May 6, 2023 issued in counterpart CN Application No. 202080077914.1.
International Search Report for counterpart International Application No. PCT/CN2020/128387.
Search report for counterpart TW Application No. 109139549 dated Sep. 14, 2021.
Search report for counterpart TW Application No. 109139549 dated Mar. 10, 2022.
Search report for counterpart EP Application No. EP20000408 dated Mar. 21, 2021.
Written Opinion of International Search Authority for counterpart International Application No. PCT/CN2020/128387.

\* cited by examiner

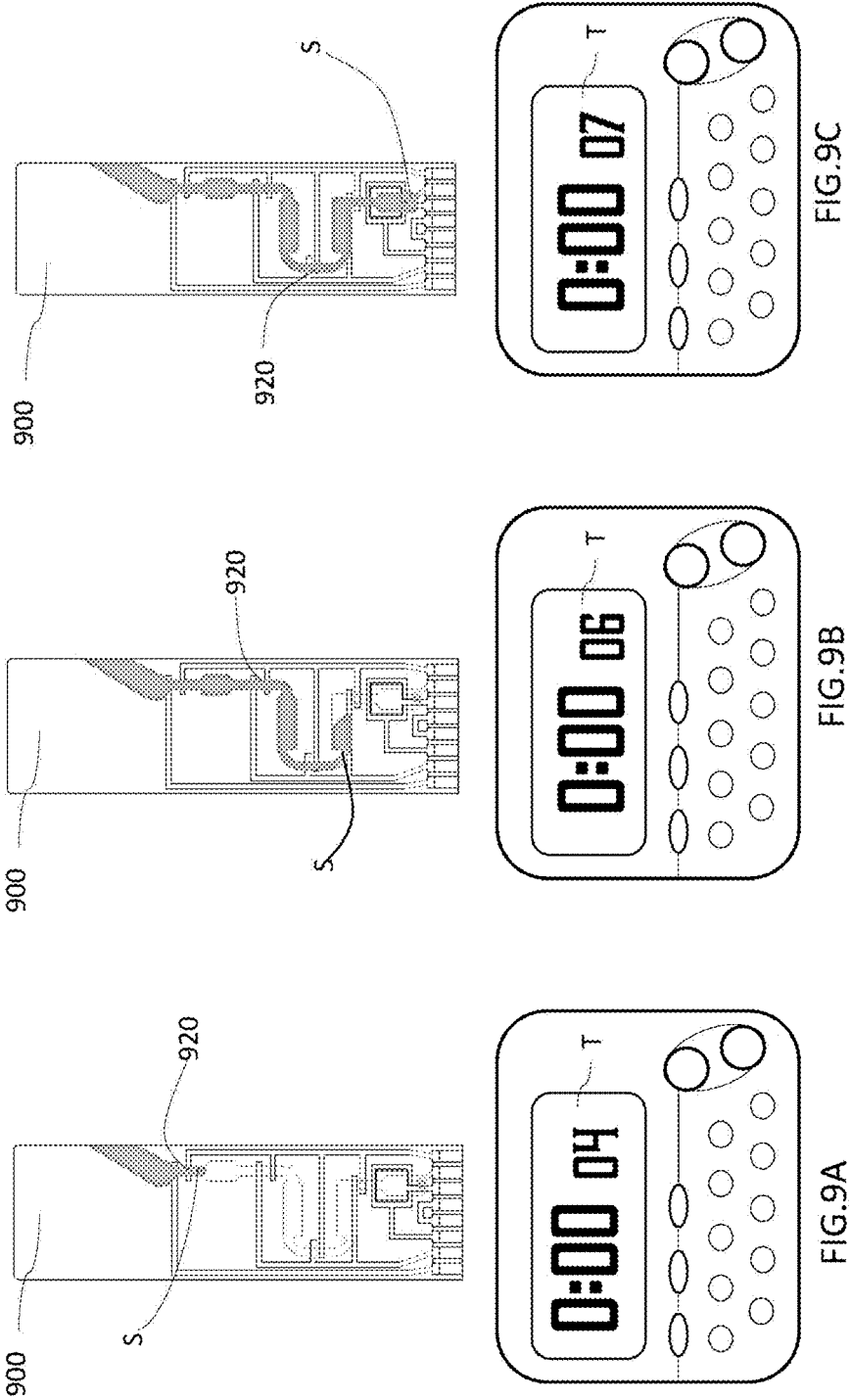

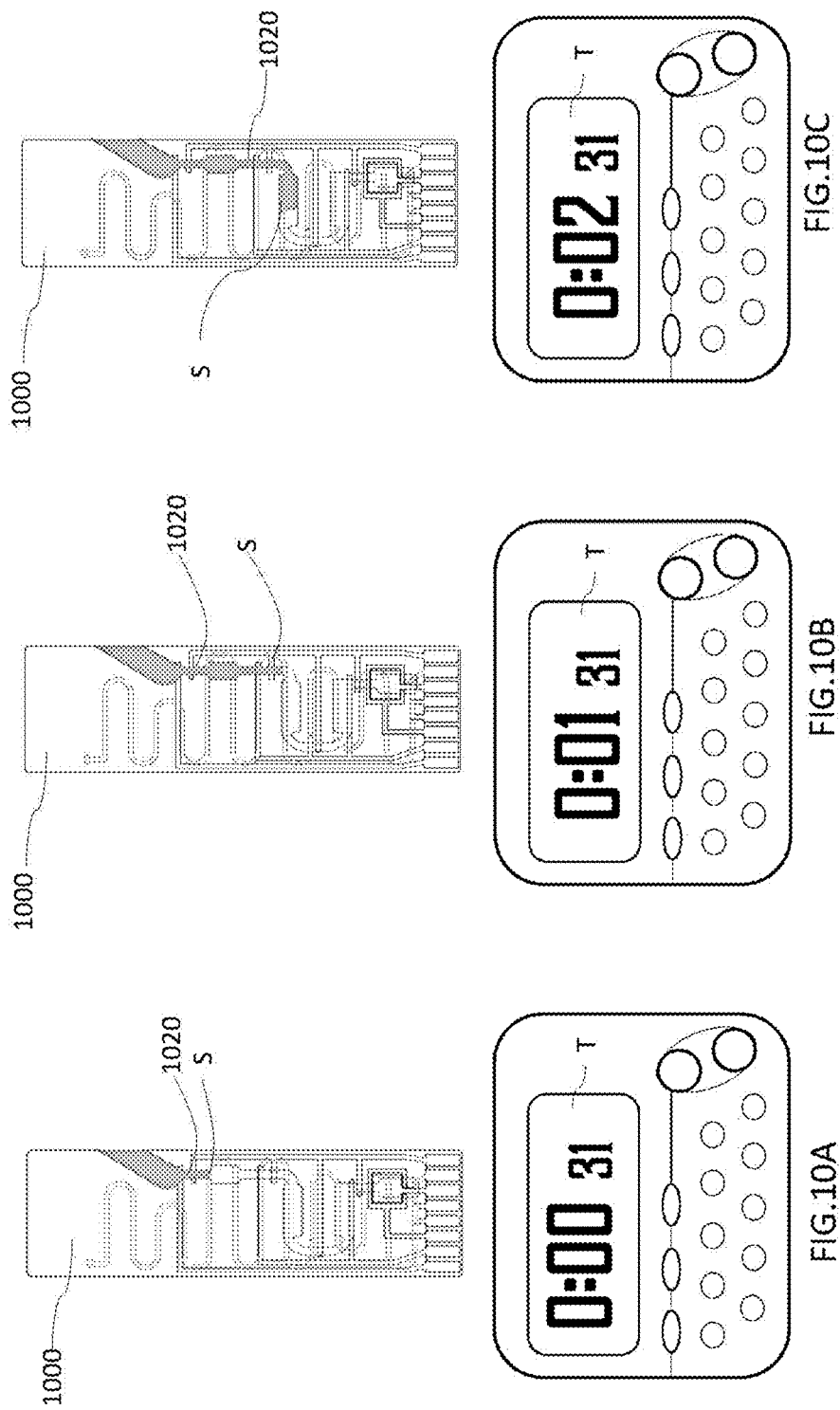

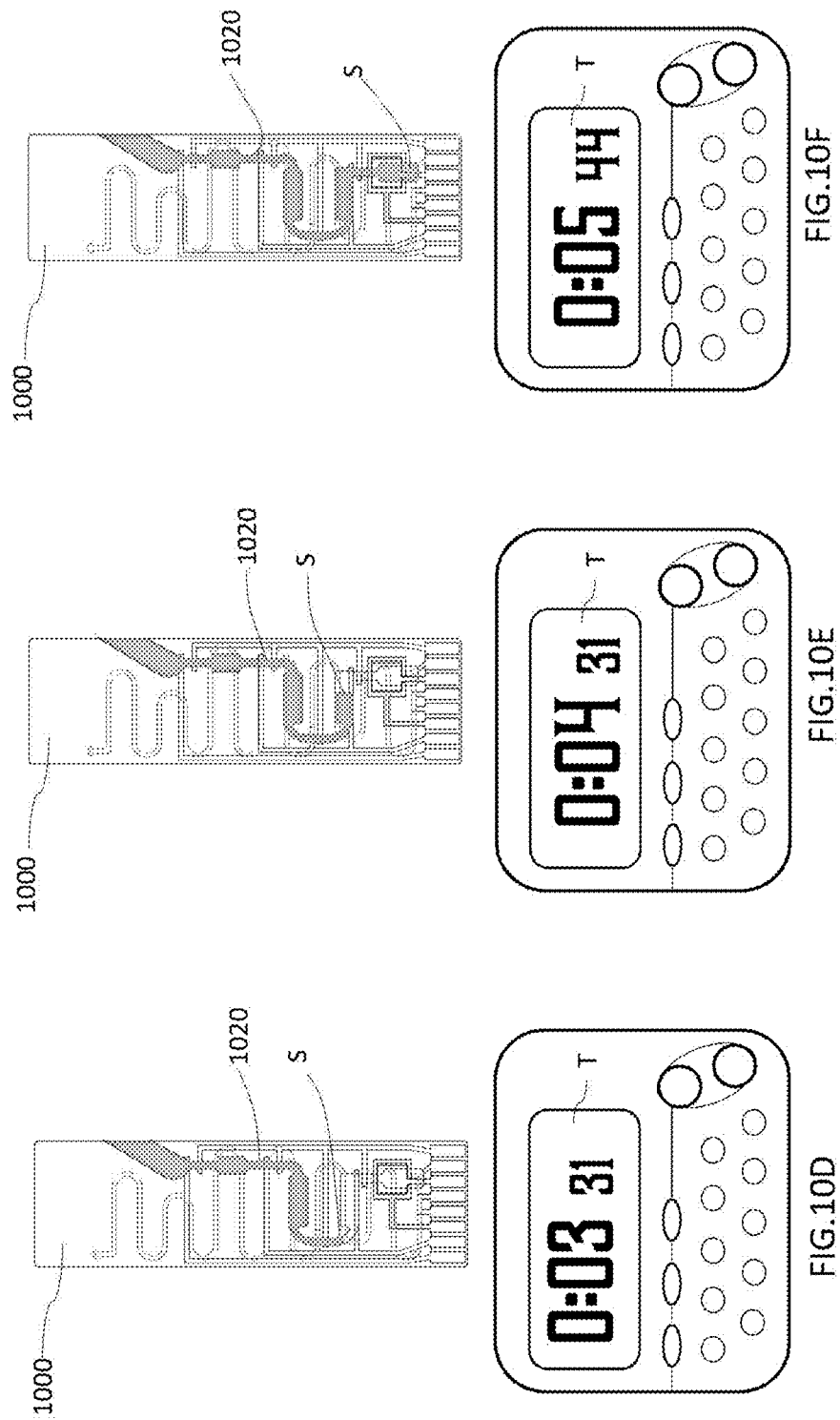

BIOSENSING TEST STRIP AND BIOSENSING TEST METHOD

FIELD OF THE INVENTION

The present invention relates to a biosensor strip, and more particularly to a biosensor strip having a controlled flow for a liquid sample.

DESCRIPTION OF THE PRIOR ART

In vitro medical measurement plays an extremely critical role in the medical industry. By qualitatively and quantitatively measuring the changes in a biological fluid, index information for quick diagnosis and treatment of diseases can be provided. In medical or biochemical testing, the use of test strips has become a common technique.

The prior art discloses a test strip that uses capillary force to absorb a liquid sample into the reaction zone. Because the capillary force of such type of test strips is affected by physical conditions such as shear stress, cohesion and viscosity of liquid samples, the flow and force of the liquid sample cannot be controlled. Thus, such a type of test strip is only suitable for simple reactions of a single agent, or multiple agents that can only act on a same position. For example, for a design requirement for a variety of agents to react in a long flow channel, such type of test strips are susceptible to non-uniform mixing due to the inability to control the flow.

The prior art also discloses a measurement carrier, which has one side of a channel thereof configured as a sampling port and the other end connected to an external power device (e.g., a pressure pump), and the effect of controlling the flow of a liquid sample is achieved by the external power device. However, the foregoing external pressuring means suffers from drawbacks of being likely to damage samples (e.g., causing blood cell rupture) and requiring high-precision bonding of seams between a flow channel and a power device.

SUMMARY OF THE INVENTION

In view of the issues of the prior art, the present invention provides a biosensor strip with a function for reducing flow of a liquid sample; more specifically, the biosensor strip has an exhaust flow channel that is configured to reduce the flow of a liquid sample provided by a capillary action.

A biosensor strip and a method thereof are provided according to an embodiment of the present invention. The biosensor strip includes a reaction layer having a reaction flow channel; a separation layer located above the reaction layer and covering the reaction flow channel; an exhaust layer located above the separation layer, the exhaust layer having an exhaust flow channel; and a through hole passing through the separation layer to communicate with the exhaust flow channel and the reaction channel.

A method for determining a structure of a biosensor strip is provided according to another aspect of the present invention. The biosensor strip has an exhaust flow channel to reduce the flow of a liquid sample in a reaction flow channel. The method obtains a structural relation between the exhaust flow channel and the reaction flow channel according to resistance parameters of the liquid sample and air.

The present invention further includes other aspects, and these features and advantages of the present invention can be better understood with reference to the accompanying drawings or using the implementations of the present invention in the description below.

BRIEF DESCRIPTION OF THE DRAWINGS

FIG. 9A, FIG. 9B and FIG. 9C are schematic diagrams of operating a conventional biosensor strip without an exhaust flow channel;

FIG. 10A, FIG. 10B, FIG. 10C, FIG. 10D, FIG. 10E and FIG. 10F are schematic diagrams of operating a biosensor strip according to an embodiment of the present invention.

DETAILED DESCRIPTION OF THE EMBODIMENTS

Preferred embodiments of the present invention are given as examples with reference to the accompanying drawings below. To avoid obscuring the contents of the present invention, details of conventional elements, associated materials and associated processing techniques are omitted from the description below.

First Embodiment

Figure 1:
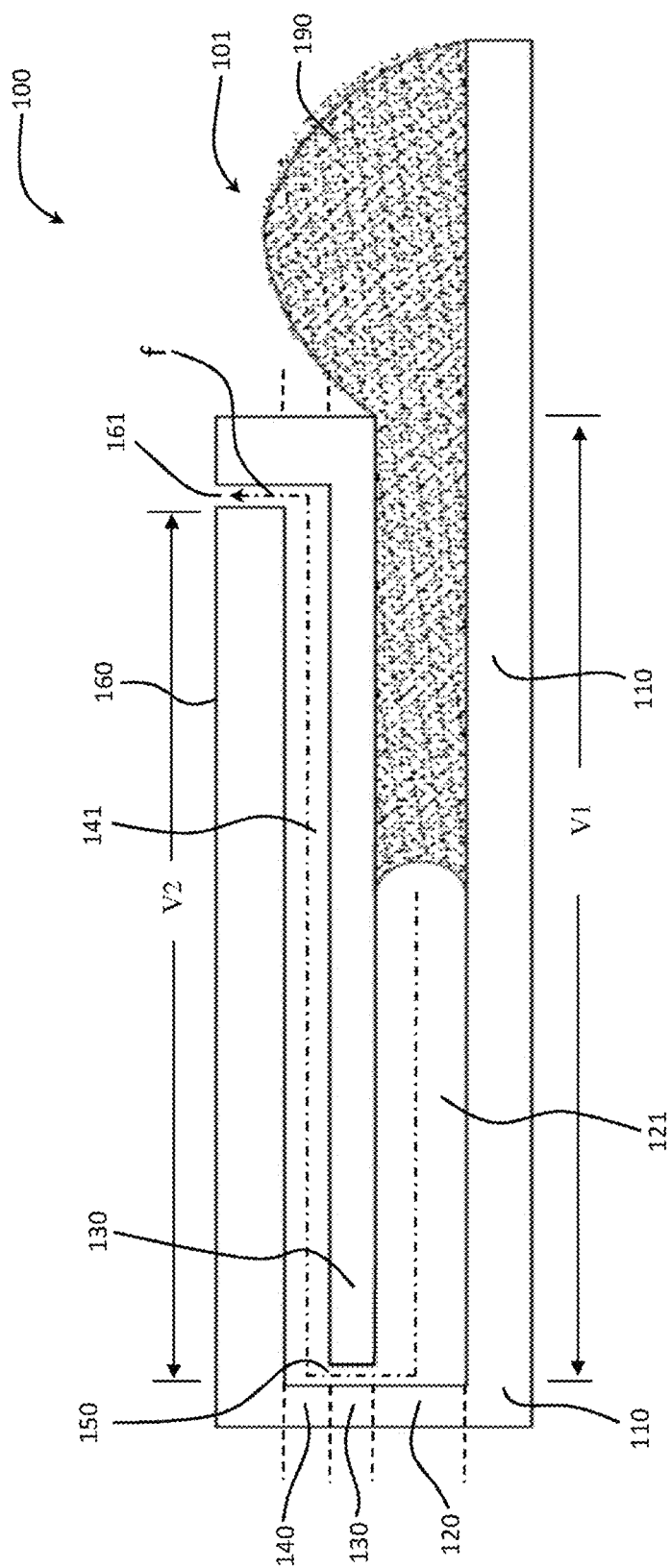
FIG. 1 is a schematic diagram of a biosensor strip according to a first embodiment of the present invention.

Referring to FIG. 1, a method for determining a structure of a biosensor strip is provided according to a first embodiment of the present invention. The method is suitable for a biosensor strip 100 in FIG. 1 showing a lateral section diagram. As shown, the biosensor strip 100 is strip-shaped, and is defined with a sampling end 101. The biosensor strip 100 includes a reaction layer 120 above a substrate layer 110, the reaction layer 120 having a reaction flow channel 121; a separation layer 130, located above the reaction layer 120 and covering the reaction flow channel 121, the reaction flow channel 121 being a space for a liquid sample 190 to flow and perform an electrochemical reaction; an exhaust layer 140, located above the separation layer 130, the exhaust layer 140 having an exhaust flow channel 141; and a through hole 150, passing through the separation layer 130 to communicate with the exhaust flow channel 141 and the reaction flow channel 121. The biosensor strip 100 further includes an upper cover 160 having an exhaust hole 161 for discharging into outside, the exhaust hole 161 being in communication with the exhaust flow channel 141. The reaction flow channel 121 has a capillary structure. The exhaust flow channel 141 has a function of reducing the flow of the liquid sample 190 provided by a capillary action. It should be noted that, this embodiment provides an illustrative example using an electrochemical strip. In other embodiments, an optical detection window can be provided on the strip. In yet other embodiments, both optics and electrochemistry can be used on the strip.

The method for determining a structure of a biosensor strip according to the first embodiment includes (1) providing the foregoing biosensor strip 100; (2) calculating a dimensionless resistance ratio μ* of the biosensor strip 100 according to formula I:

$$\mu^* = \frac{\mu_G}{(\mu_L - \mu_G)} \quad \text{formula I}$$

where $\mu_G$ is the resistance of air in the exhaust flow channel, and $\mu_L$ is the resistance of a liquid sample 190 used in the biosensor strip; (3) determining a numeral value greater than the dimensionless resistance ratio μ*; and (4) considering the numeral value as a dimensionless length ratio L*, and substituting L* into formula II below to obtain a structural relation between the reaction flow channel 121 and the exhaust flow channel 141:

$$L^* = \frac{L_L w_G h_G^3 C_G}{L_G w_L h_L^3 C_L}, \quad \text{formula II}$$

where $w_L$ is wall width of the reaction flow channel 121, $h_L$ is the wall height of the reaction flow channel 121, $L_L$ is the length of the reaction flow channel 121, $C_L$ is a rectangle correction coefficient of the reaction flow channel 121, $w_G$ is the wall width of the exhaust flow channel 141, $h_G$ is the wall height of the exhaust flow channel 141, $L_G$ is the length of the exhaust flow channel 141, and $C_G$ is a rectangle correction coefficient of the exhaust flow channel 141; wherein, $C_L$ or $C_G$ are respectively obtained according to formula III below:

$$C = \left[1 - \sum_{n,odd}^{\infty} \frac{192}{\pi^5} \frac{h}{w} \frac{1}{n^5} \tan h\left(n\pi \frac{w}{2h}\right)\right], \quad \text{formula III}$$

where w is the wall width of the reaction flow channel 121 or the exhaust flow channel 141, and h is the wall height of the reaction flow channel 121 or the exhaust flow channel 141. Sources of the formulae above are explained below. It should be noted that the method above takes the biosensor strip 100 as an example. The method above is also suitable for other biosensor strips according to other embodiments of the present invention.

The volume of the liquid sample 190 that the biosensor strip 100 can accommodate depends on the shape of the reaction flow channel 121. The reaction flow channel 121 is an elongated pipeline surrounded on four sides, and an approximate formula the flow $Q_L$ of the liquid sample 190 therein is:

$$Q_L = \frac{\Delta P w_L h_L^3}{12 \mu_L L_L},$$

where is the wall width of the reaction flow channel 121, $h_L$ is the wall height of the reaction flow channel 121, μL is the viscosity of the liquid sample 190, $L_L$ is the length of the reaction flow channel 121, and ΔP is the capillary pressure of the liquid sample 190 in the reaction flow channel 121. Without considering the pressure difference of the distance of the flow channel, the calculation formula for $\Delta P_L$ is approximately:

$$\Delta P_L = \frac{\gamma \cos\theta (2w_L + 2h_L)}{w_L h_L},$$

where γ is the liquid surface tension, and θ is the contact angle of the liquid sample 190 with respect to the surface of the reaction flow channel 121.

The flowing of the air in the biosensor strip 100 is mainly caused by the force exerted by the liquid sample 190. In other words, while capillary action is applied, the flowing of the liquid sample 190 in the reaction flow channel 121 needs to push air in order to move forward. An arrow fin FIG. 1 shows the flowing direction of pushed air. Under the effects applied by the wall of the reaction flow channel 121 onto the liquid sample 190 and air, given that the reaction flow channel 121 connects the exhaust flow channel 141 in series and that the air flow $Q_G$ is significantly smaller than the flow $Q_L$ of the liquid sample 190, the air flow controls the flow of the liquid sample 190. In brief, the flowing speed of air can be controlled by air resistance generated by the exhaust flow channel 141 while the flow of the liquid as well as the bio(electro)chemical reaction time can be controlled simultaneously.

A calculation formula of the air flow in the inner wall of a common exhaust flow channel is:

$$Q_G = \frac{\Delta P w_G h_G^3 C}{12 \mu_G L_G},$$

where $w_G$ is the wall width of the exhaust flow channel, $h_G$ is the wall height of the exhaust flow channel, $\mu_G$ is the viscosity of air, $L_G$ is the length of the exhaust flow channel, and C is a rectangle correction coefficient, which is the resistance coefficient generated by a rectangle flow channel with respect to flowing of air and can be calculated by the formula below:

$$C = \left[1 - \Sigma_{n,odd}^{\infty} \frac{192}{\pi^5} \frac{h}{w} \frac{1}{n^5} \tan h\left(n\pi \frac{w}{2h}\right)\right].$$

The exhaust flow channel has a lateral cross section perpendicular to an extension direction of the exhaust flow channel. To calculate by bringing various length-to-width ratios of different lateral cross sections into the above formula of the rectangle correction coefficient, it is obtained that an exhaust flow channel with rectangular cross section has less influence than that with a square cross section. Thus, it is deduced that the exhaust flow channel preferably has a lateral cross section having a long diameter and a short diameter. In a preferred embodiment, a ratio of the long diameter to the short diameter is greater than 2, more preferably greater than 6, and most preferably greater than 8.

It is known from the calculation formula of air flow above that, the length of the exhaust flow channel 141 is crucial to producing effect of air resistance upon the liquid sample 190. As shown in FIG. 1, the volume of the exhaust flow channel 141 is V2, and the volume of the reaction flow channel 121 is V1. Before the liquid sample 190 is injected to the sampling port 101, air fills the reaction flow channel 121 and the exhaust flow channel 141. The liquid sample 190 is affected by the air resistance from the moment it enters the reaction flow channel 121 caused by the resulted capillary action. Thus, the volume V1 of the reaction flow channel 121 and the volume V2 of the exhaust flow channel 141 are taken into account when the overall effect of air resistance is calculated. Therefore, the calculation formula for the total air flow of the biosensor strip 100 should be:

$$Q_{GT} = \frac{Q_{GV1} Q_{GV2}}{Q_{GV1} + Q_{GV2}},$$

where $Q_{GT}$ is the total air flow, $Q_{GV1}$ is the air flow of the reaction flow channel 121, and $Q_{GV2}$ is the air flow of the exhaust flow channel.

However, because the cross-section area of the reaction flow channel 121 is far greater than the cross section of the reaction flow channel 141, the air flow of the reaction flow channel 121 is also driven by the air flow of the exhaust flow channel 141, such that the air flow $Q_{GV1}$ of the reaction flow channel 121 can be omitted in the calculation for the total air flow $Q_{GT}$. Therefore, the calculation formula for the total air flow can be corrected to:

$$Q_{GT} \approx Q_{GV2}.$$

The viscosities of various liquid samples will change the air flow $Q_G$. Therefore, in this embodiment, in order to minimize the influence on the air flow $Q_G$ caused by the viscosities of various liquid samples, the relation of the resistance contributed by the flow channels, the viscosity of the liquid sample and the viscosity of air should be considered, as follows:

$$R_G > \Delta R_L \rightarrow \frac{12\mu_G L_G}{w_G h_G^3 C_G} > \frac{12(\mu_L - \mu_G)L_L}{w_L h_L^3 C_L}$$

$$\frac{\mu_G}{(\mu_L - \mu_G)} > \frac{L_L w_G h_G^3 C_G}{L_G w_L h_L^3 C_L} \leftrightarrow \mu^* > L^*,$$

where $R_G$ is the resistance of air in the exhaust flow channel 141, $\Delta R_L$ is the resistance difference between the liquid sample 190 and the air in the reaction flow channel 121, $C_G$ and $C_L$ are respectively rectangle correction coefficients of the exhaust flow channel 141 and the reaction flow channel 121, $\mu^*$ is a dimensionless resistance ratio, and $L^*$ is a dimensionless length ratio.

It is known from the above, the biosensor strip 100 satisfying the condition of the dimensionless resistance ratio $\mu^*$ being greater than the dimensionless length ratio $L^*$ ensures that the resistance generated by the air and the liquid sample 190 in the reaction flow channel 121 is smaller than the resistance generated by air in the exhaust flow channel 141, thereby achieving the air flow $Q_G$ far smaller than the liquid sample flow $Q_L$. However, the present invention does not define the difference between $\mu^*$ and $L^*$, preferably, the ratio difference between $\mu^*$ and $L^*$ is 5 times, more preferably, the ratio difference between $\mu^*$ and $L^*$ is 20 times, and most preferably, the ratio difference between $\mu^*$ and $L^*$ is 100 times. In another embodiment, to reduce the interference of ambient temperature on the control for the flow of the liquid sample 190, a heater applied for the biosensor strip 100 can be configured in a measuring device (not shown), so as to ensure that each time the biosensor strip 100 is used, the pressure in the reaction flow channel 121 or the exhaust flow channel 141 stays the same.

The formulae above are suitable for some embodiments. However, for some other embodiments, for example, when the viscosity of a liquid sample is extremely large such that the formulae above are inapplicable, adjustment can be made by, for example, the method of the second embodiment below.

Second Embodiment

Figure 2:
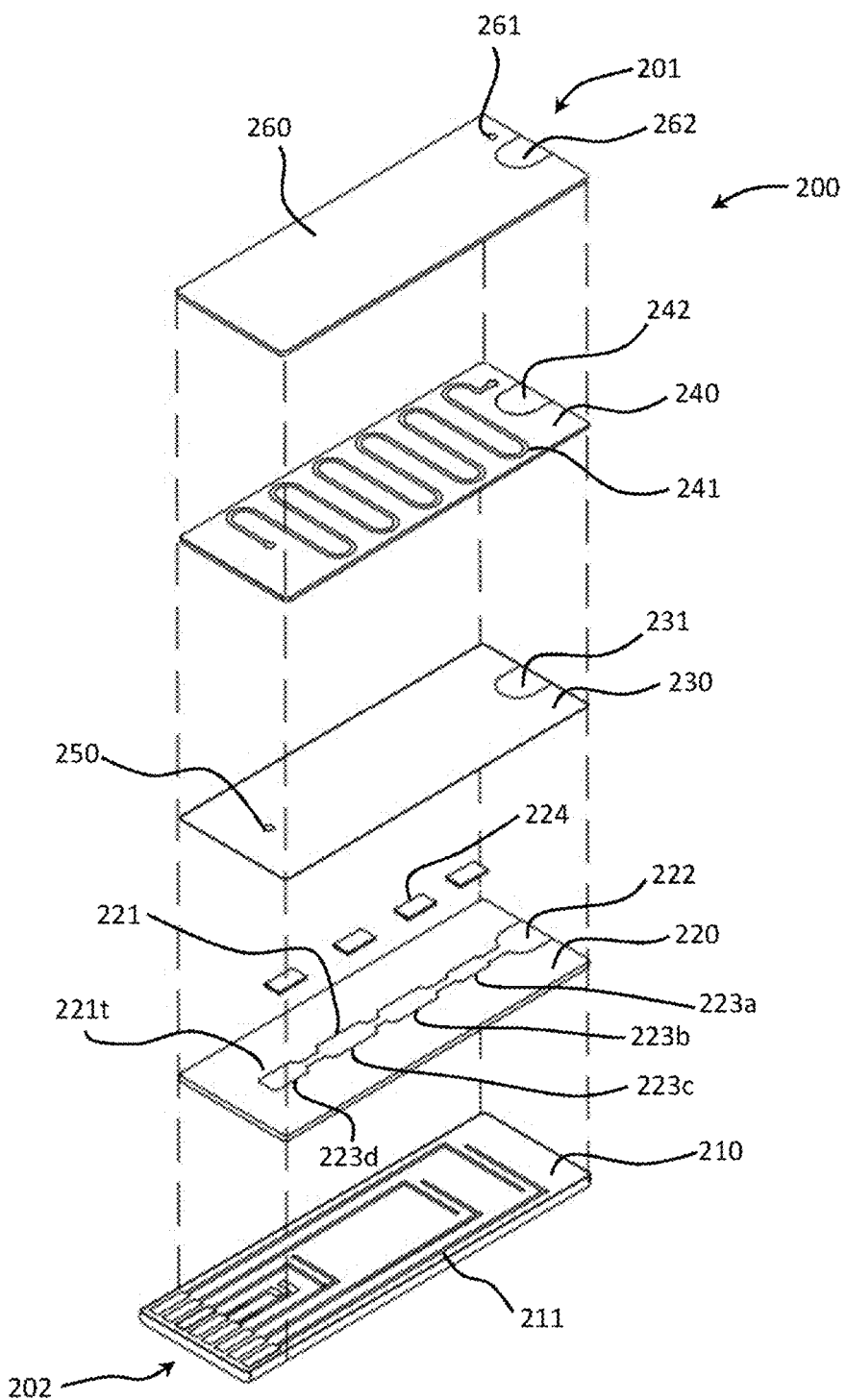
FIG. 2 is a schematic diagram of a biosensor strip according to a second embodiment of the present invention.

FIG. 2 shows an exploded schematic diagram of the components of a biosensor strip 200 according to the second embodiment. The biosensor strip 200 is strip-shaped, and is defined with a sampling end 201 and a connecting end 202, wherein the connecting end 202 is for electrically connecting to a measuring device (not shown). Referring to FIG. 2, the biosensor strip 200 includes a reaction layer 220 above a substrate layer 210, the reaction layer 220 having a reaction channel 221; a separation layer 230, located above the reaction layer 220 and covering the reaction flow channel 221; an exhaust layer 240, located above the separation layer 230, the exhaust layer 240 having an exhaust flow channel 241; and a through hole 250 passing through the separation layer 230 to communicate with the exhaust flow channel 241 and the reaction flow channel 221. The biosensor strip 200 further includes an upper cover 260 having an exhaust hole 261 for discharging into outside and communicating with the exhaust flow channel 241. In another embodiment, the exhaust hole (not shown) is provided on the exhaust layer 240. The design details (for example, sizes of the channel or holes for the components) with respect to the reaction flow channel 221, the through hole 250 and the exhaust flow channel 241 can be referred from the method of the first embodiment. In this embodiment, the reaction flow channel 221 is also a capillary structure, and the exhaust flow channel 241 has a function of reducing the flow of the liquid sample 190 provided by a capillary action.

Referring to FIG. 2, the substrate layer 210, the reaction layer 220, the separation layer 230, the exhaust layer 240 and the upper cover 260 above are formed in general of an insulation material, and can be one selected from a group consisting of polyvinyl chloride (PVC), glass fiber (FR-4), polyester (polyester suphone), bakelite, polyethylene terephthalate (PET), polycarbonate (PC), polypropylene (PP), polyethylene (PE), polystyrene (PS), glass plate and ceramic, or any combination thereof. The layers are sequentially combined as shown to form the biosensor strip 200.

Referring to FIG. 2, the substrate layer 210 further includes an electrode unit 211 configured on the substrate layer 210. The electrode unit 211 can be consisted of at least one group of mutually insulated electrodes. The material of the electrode unit 211 can be any electrically conductive substance, such as palladium glue, platinum glue, gold glue, titanium glue, carbon glue, silver glue, copper glue, gold and silver mixed glue, carbon silver mixed glue, or any combination of these electrically conductive materials.

Referring to FIG. 2, the reaction flow channel 221 of the reaction layer 220 has a sampling port 222 located on the sampling end 201. A liquid sample suitable for the present invention is usually blood; however, the present invention is not limited thereto. Four reagent areas 223a, 223b, 223c and 223d are arranged along the reaction flow channel 221 in the direction of the liquid sample entering the reaction flow channel 221 from the sampling port, and are individually placed with the same or various different reagents 224. A region having a larger area on the reaction flow channel 221 is for the purpose of moderating the flow of the liquid sample in that region. The liquid sample stays in a region having a larger area for a relatively longer period of time. A reagent can be placed in a region having a larger area; however, the present invention is not limited thereto. The present invention includes other embodiments having various numbers of reagent area, including only one reagent area. The reagent suitable for the present invention includes enzymes (e.g., glucose glucoamylase), conductive media (such as red blood salt), phosphate buffer, protective agents (such as proteins, dextrin, glucosan, amino acids, etc.), and also includes components with biological identification capabilities such as antigens, antibodies, microbial cells, animal and plant cells, and animal and plant tissues. FIG. 2 shows that the reaction flow channel 221 is a linear path; however, the present invention also includes other embodiments in which the reaction flow channel 221 is in other path shapes. As shown in FIG. 2, in this embodiment, when the liquid sample enters the reaction flow channel 221 form the sampling end 222, air in the reaction flow channel 221 flows toward a terminal end 221$t$, and air in the exhaust flow channel 241 also flows toward the direction of the exhaust hole 261.

Referring to FIG. 2, the separation layer 230 has on the side of the sampling end 201 a first notch 231 corresponding to the sampling port 222. The through hole 250 passes through the separation layer 230 at a side of near the terminal end 221$t$. The separation layer 230, the inner wall of the reaction layer 220 and the substrate layer 210 jointly form the space of the reaction flow channel 221, wherein the separation layer 230 constitutes the upper wall of the reaction flow channel 221, the substrate layer 210 constitutes the bottom wall of the reaction flow channel 221, and the inner wall of the reaction layer 220 constitutes the sidewall of the reaction flow channel 221. In one embodiment, at least one wall surface of the reaction flow channel 221, preferably, at least one wall surface located on the bottom wall or the upper wall of the reaction flow channel 221, is hydrophilic. In another embodiment, compared to the bottom wall or the upper wall of the reaction flow channel 221, the hole wall of the through hole 250 is more hydrophobic. According to FIG. 2, with respect to the starting end (the position of the sampling port 222) of the reaction flow channel 221, the through hole 250 corresponds to the terminal end 221$t$ of the reaction flow channel 221. That is, air from the reaction flow channel 221 flows through the last reagent area 223$d$ and then arrives at the through hole 250. In other embodiments, the position of the through hole 250 can correspond to other appropriate position of the reaction flow channel 221.

Referring to FIG. 2, the exhaust layer 240 has on the side of the sampling end 201 a second notch 242 corresponding to the first notch 231 and the sampling port 222. FIG. 2 shows that the exhaust flow channel 241 is distributed in a wave manner on the exhaust layer 240; however, the present invention also includes embodiments in which the reaction flow channel is in other shapes, including shapes of a straight line, a digital wave, a sawtooth, a triangular wave and various irregular curves.

Referring to FIG. 2, the upper cover 260 has on the side of the sampling end 201 a third notch 262 corresponding to the second notch 242, the first notch 231 and the sampling port 222. The upper wall 260, the inner wall of the exhaust layer 240 and the separation layer 230 jointly form the space of the exhaust flow channel 241, wherein the upper cover 260 constitutes the upper wall of the exhaust flow channel 241, the separation layer 230 constitutes the bottom wall of the exhaust flow channel 241, and the inner wall of the exhaust layer 240 constitutes the sidewall of the exhaust flow channel 241. In another embodiment, the size of the third notch 262 is smaller than that of the sampling port 222. In other embodiments, the size of the first notch 231 or the second notch 242 can be smaller than the sampling port 222.

Third Embodiment

Figure 3:
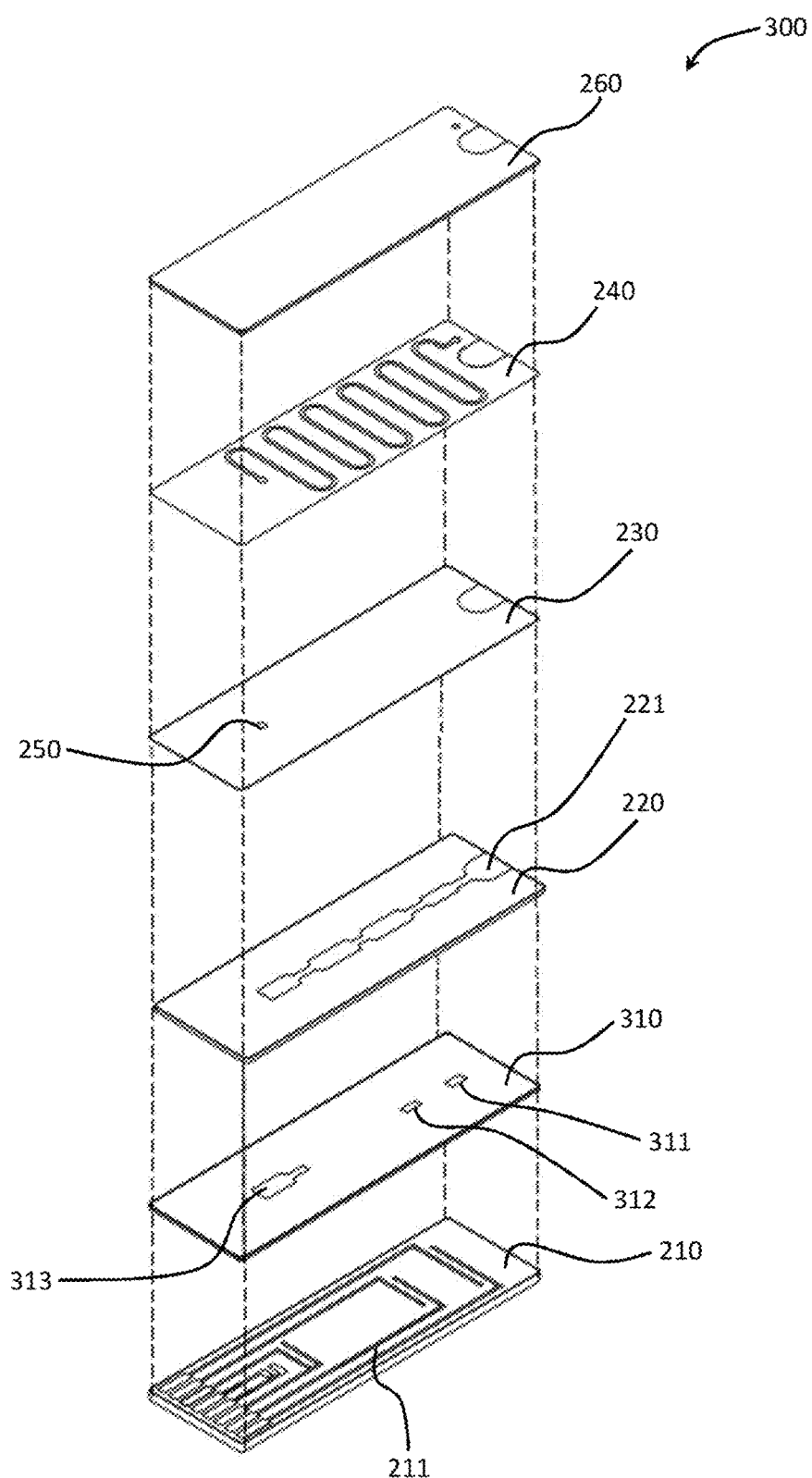
FIG. 3 is a schematic diagram of a biosensor strip according to a third embodiment of the present invention.

FIG. 3 shows an exploded schematic diagram of the components of a biosensor strip 300 of the third embodiment. The biosensor strip 300 is similar to the biosensor strip 200 of the second embodiment, and differs in that the biosensor strip 300 further includes a hydrophilic layer 310. The hydrophilic layer 310 has a first exposure opening 311, a second exposure opening 312 and a third exposure opening 313 for exposing electrodes underneath the substrate layer 210. The function of the hydrophilic layer 310 is to reduce the contact angle between the liquid sample in the reaction flow channel 221 and the channel surface so as to achieve an effect of stabling flow. The third embodiment can be used for cases where the hydrophilic ability of the substrate layer 210 is insufficient in need. For example, the change in hydrophilicity on the surface of the substrate 210 is restrained by placing the necessary electrode unit 211 thereon. In this embodiment, the flow of a common liquid sample in the reaction flow channel 221 is controlled by the exhaust flow channel 241. However, the flow of certain high-viscosity liquid samples in the reaction flow channel 221 could be slower than the expected flow controlled by the exhaust flow channel, resulting in a flow error in the flow controlled by the exhaust flow channel 241. Such unfavorable situations can be alleviated or even avoided by means of the hydrophilic layer 310.

Fourth Embodiment

Figure 4A:
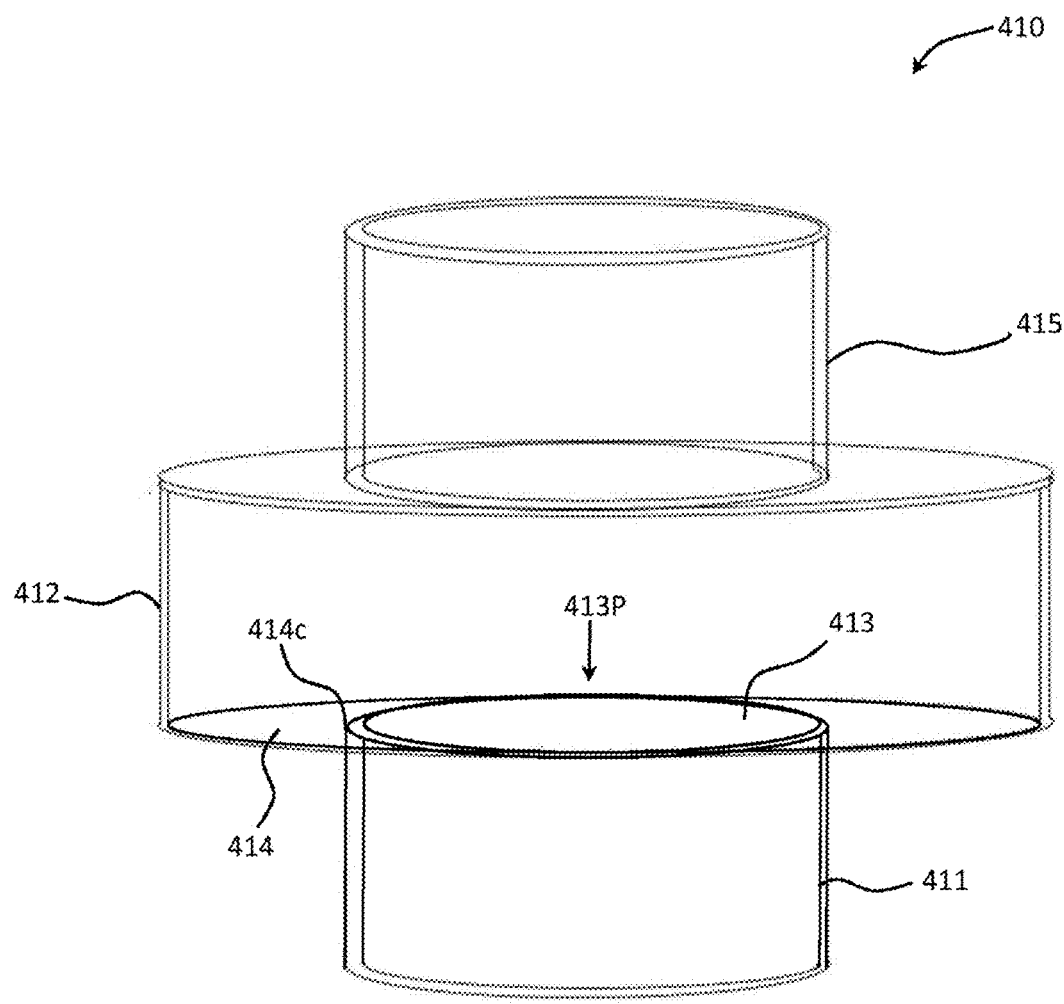
FIG. 4A and FIG. 4B are schematic diagrams of a choke valve of a biosensor strip according to a fourth embodiment of the present invention.
Figure 4B:
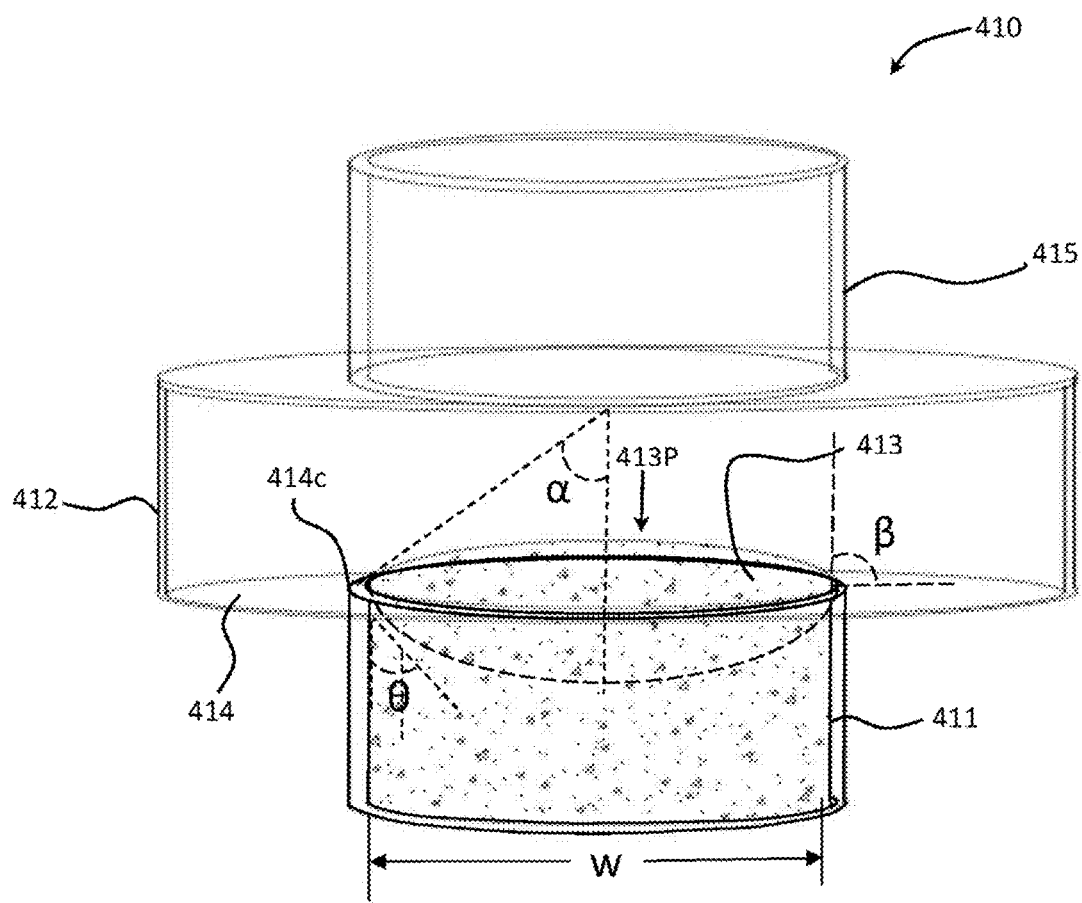

FIG. 4A and FIG. 4B are section perspective schematic diagrams of a choke valve 410 of a biosensor strip of the fourth embodiment, wherein FIG. 4A does not depict a liquid sample whereas FIG. 4B depicts a liquid sample. Details of the other components of the fourth embodiment can be referred from the second embodiment or the third embodiment. The choke valve 410 is disposed in the through hole 250. In other words, referring to the second embodiment or the third embodiment, the choke valve 410 is located at the through hole 250 corresponding to the terminal end 221$t$ of the reaction flow channel 221 and passes through the separation layer 230. In this embodiment, the choke valve 410 can prevent overflow of the liquid sample from entering the exhaust flow channel 241.

Referring to FIG. 4A, the choke valve (through hole) 410 has a lower slot 411 in communication with the reaction flow channel 221, and a middle slot 412 located above the lower slot 411. The lower slot 411 has an opening 413 in communication with the middle slot 412, and the opening 413 is defined with a horizontal plane 413$p$. The middle slot 412 has a bottom part 414, the bottom part 414 has a connecting part 414$c$ connected to the opening 413, and a surface of the connecting part 414$c$ is not higher than the horizontal plane 413$p$, such that the liquid sample from the lower slot 411 has no access to a clinging wall surface so as to achieve a flow stop effect.

Referring to FIGS. 4A and 4B, the size of the middle slot 412 is greater than the size of the lower slot 411. Moreover, the choke valve 410 further includes an upper slot 415 in communication with the middle slot 412, and the size of the upper slot 415 is preferably smaller than or equal to that of the middle slot 412, or preferably smaller than or equal to that of the lower slot 411. The height of the middle slot 412 is higher than the maximum height of the liquid sample 190 at the opening 413, so as to further prevent the liquid sample 190 from entering the upper slot 415 or the exhaust flow channel 241. In other embodiments, the choke valve 410 may exclude the upper slot 412. In this embodiment, the upper slot 415 of the choke valve 410 is located at the exhaust layer 240, the middle slot 412 of the choke valve 410 is located at the separation layer 230, and the lower slot 411 of the choke valve 410 is located at the reaction layer 220. In another embodiment, the middle slot 412, the lower slot 411 and the upper slot 415 (if any) can all be located at the separation layer 230. In another embodiment, the through hole 250 can include two or more vertically overlaid choke valves 410.

Moreover, in another embodiment, the surface of the connecting part 414c forms a hydrophobic surface. The flow stop effect of the choke valve 410 can be reinforced by the hydrophobic surface as the surface of the connecting part 414c is described with reference to FIG. 4B and the formula below. For example, as the hydrophobic ability of the surface of the connecting part 414c gets higher, the liquid sample is less likely to approach the surface of the connecting part 414c such that the wavefront of the liquid sample rises:

$$\Delta P_c = \frac{2\gamma_{la}}{W}\left(\frac{\cos\theta - \frac{\alpha}{\sin\alpha}\sin\beta}{\cos\beta + \frac{\sin\beta}{\sin\alpha}\left(\frac{\alpha}{\sin\alpha} - \cos\alpha\right)}\right).$$

A flow channel border is defined as an intersection of the opening 413, the wall of the lower slot 411 and the surface of the connecting part 414c. $\Delta P_c$ is a liquid pressure at the wall of a flow channel border (i.e., the pressure of the liquid sample leaning against the lower slot 411 when located at the opening 413), $\gamma_{la}$ is a surface tension coefficient of the liquid sample, w is the width of the lower slot 411, θ is the contact angle between the liquid sample and the wall of the lower slot 411, α is a wavefront arc of the liquid sample and the flow channel border, and β is the contact angle between the opening 413 and the connecting part 414c. Thus, $\Delta P_c$ can be controlled by adjusting β. β is merely 0°≤β<90°. When the angle β is 90°, $\Delta P_c$ is smaller; however, a flow stop effect can be more easily achieved. In addition, when the relation ($\Delta P_L$) of liquid pressure at the wall of the flow channel border and the capillary pressure of the liquid sample at the lower slot 411 satisfies $\Delta P_c = \Delta P_L$, the liquid sample in the lower slot 411 stops moving upward.

Fifth Embodiment

Figure 5:
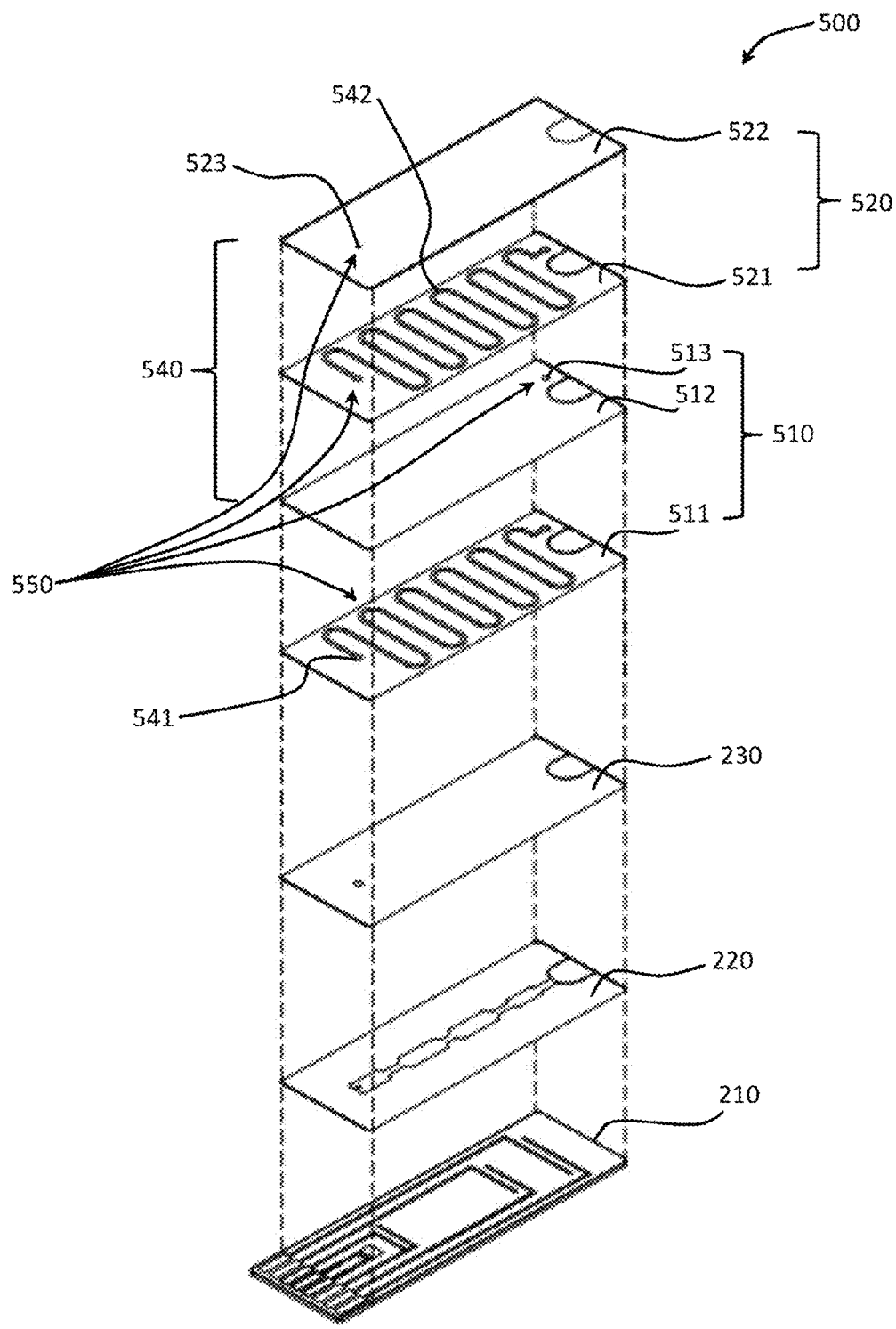
FIG. 5 is a schematic diagram of a biosensor strip according to a fifth embodiment of the present invention.

FIG. 5 shows an exploded schematic diagram of the components of a biosensor strip 500 of the fifth embodiment. The biosensor strip 500 is similar to the biosensor strip 200 of the second embodiment, and differs in respect of a different exhaust layer. The exhaust layer 240 of the biosensor strip 200 has only one layer of air flow channel, whereas an exhaust layer has two layers of air flow channels. As shown, an exhaust layer 540 of the biosensor strip 500 includes a first exhaust set 510, which has a first air flow channel 541 at a first layer 511, a first upper cover 512 covering the first layer 511, and a connecting hole 513 located at the first upper cover 512; and a second exhaust set 520 disposed above the first exhaust set 510, the second exhaust set 520 having a second air flow channel 542 at a second layer 521, a second upper cover 522 covering the second layer, and an exhaust hole 523 located above the second upper cover 522. The first air flow channel 541, the connecting hole 513, the second air flow channel 542 and the exhaust hole 523 form an exhaust flow channel 550. In this embodiment, the first air flow channel 541 and the second air flow channel 542 have the same flow channel pattern. In other embodiments, the first air flow channel 541 and the second air flow channel 542 have different flow channel patterns.

Sixth Embodiment

Figure 6A:
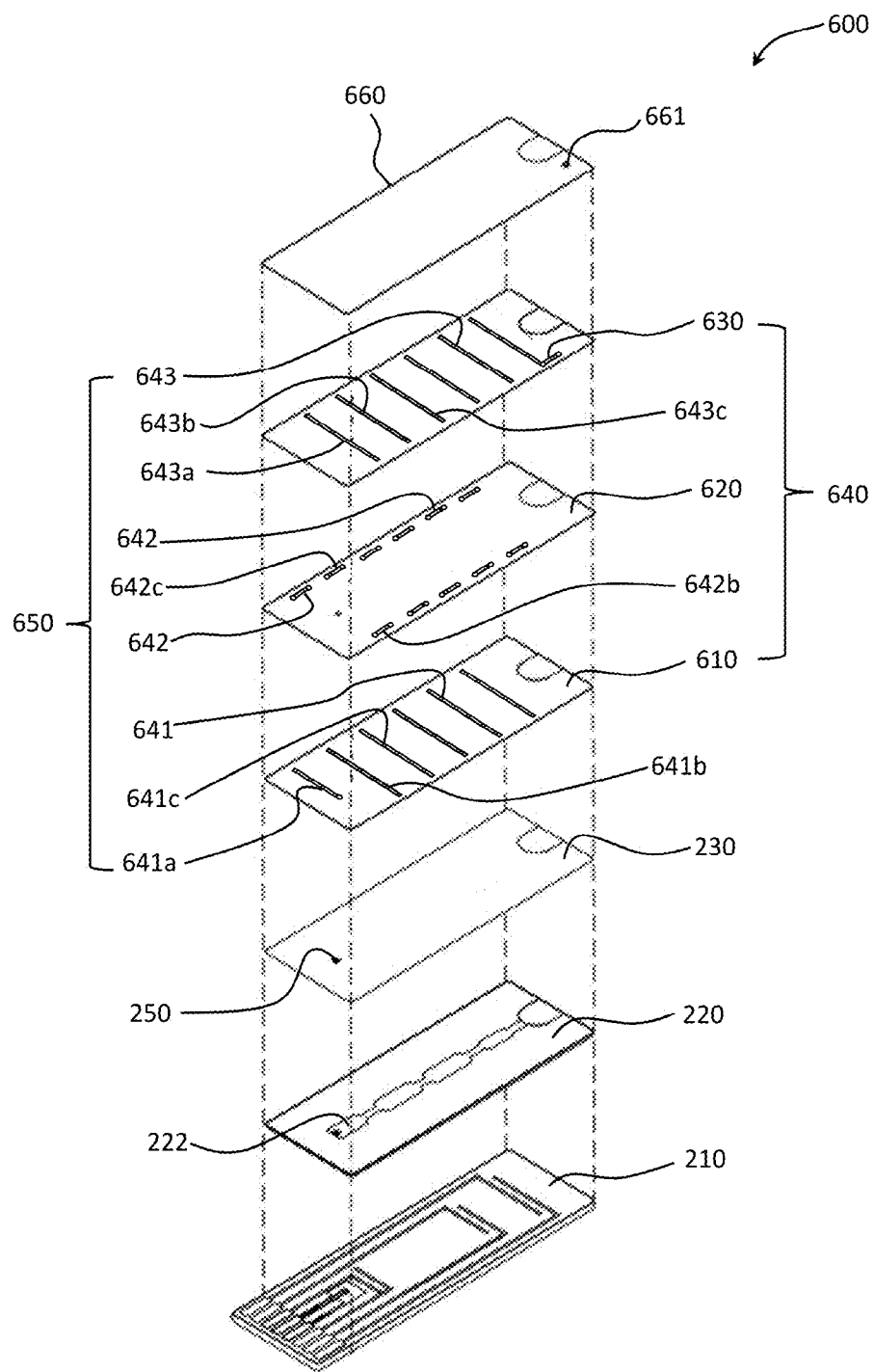
FIG. 6A and FIG. 6B are schematic diagrams of a biosensor strip according to a sixth embodiment of the present invention.
Figure 6B:
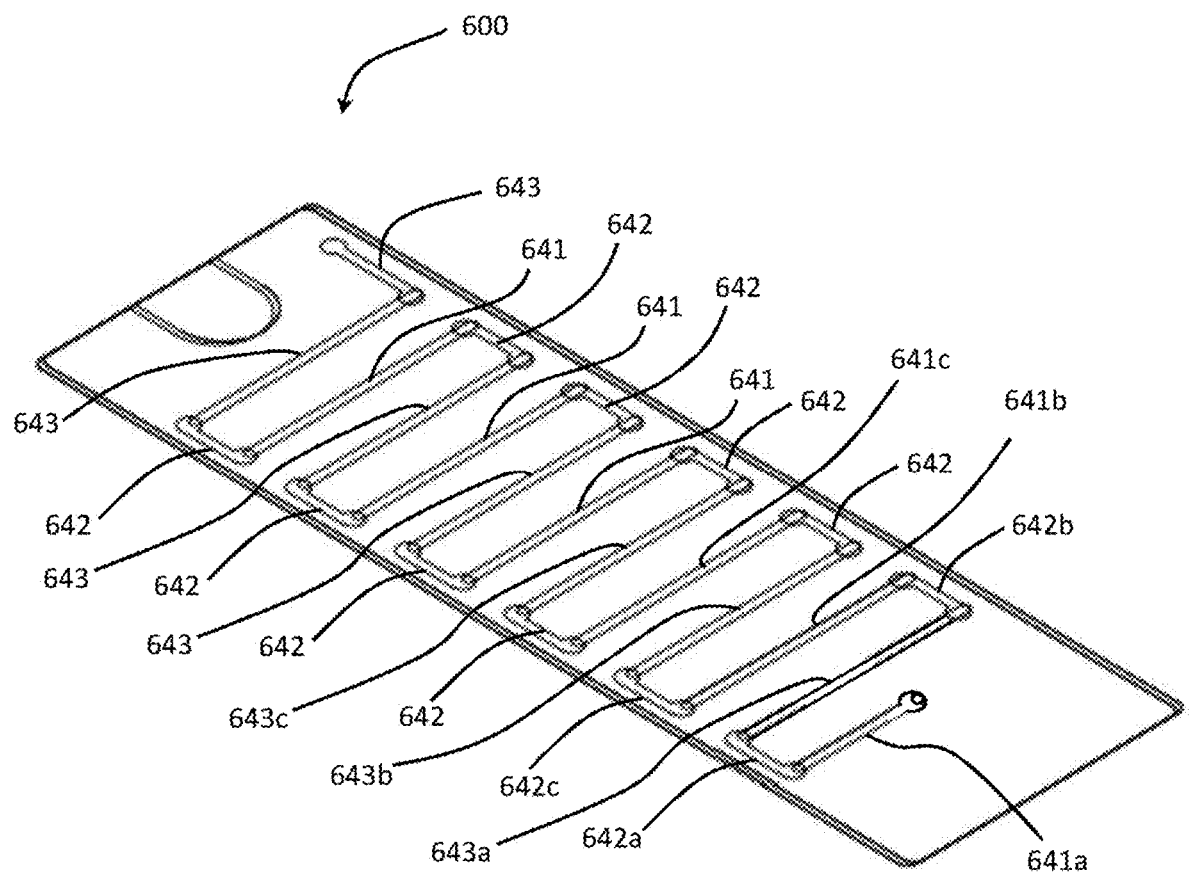

FIG. 6A shows an exploded schematic diagram of the components of a biosensor strip 600 of the sixth embodiment. FIG. 6B shows a top-viewed perspective diagram (with the components overlaid) of an exhaust layer 640 of the biosensor strip 600 of the sixth embodiment. The biosensor strip 600 is similar to the biosensor strip 200 of the second embodiment, and differs in respect of a different exhaust layer. The exhaust layer 240 of the biosensor strip 200 has only one layer of air flow channel, whereas an exhaust layer of the fifth embodiment has three layers of air flow channels. Referring to both FIGS. 6A and 6B, the exhaust layer 640 includes a first layer 610, a second layer 620 covering the first layer 610, and a third layer 630 overing the second layer 620. The exhaust layer 640 further includes a first air flow channel 641 distributed at the first layer 610, a second air flow channel 642 distributed at the second layer 620, and a third air flow channel 643 distributed at the third layer 630. The first air flow channel 641, the second air flow channel 642 and the third air flow channel 643 form the exhaust flow channel 650. When a liquid sample enters the reaction flow channel 222, the flow direction of the air in the exhaust flow channel 650 includes the following sequences: (1) flowing from the first layer 610, passing through the second layer 620 and entering the third layer 630; (2) then flowing from the third layer 630, passing through the second layer 620 and returning to the first layer 610; and (3) again flowing from first layer 610, passing through the second layer 620 and entering the third layer 630. The flow direction of the air in the exhaust flow channel 650 further includes repeating the sequences (2) and (3) and staying at the sequence (3). The biosensor strip 600 further includes an upper cover 660 covering the exhaust layer 640. The upper cover 660 has an exhaust hole 661, and the flow direction of the air in the exhaust flow channel 650 further includes, after the sequence (3), leading to the exhaust hole 661 of the upper cover 660 for discharging into outside. It can be understood with reference to FIG. 6A that the first air flow channel 641 cannot directly communicate to the third air flow channel 643; instead, the first air flow channel 641 communicates to the third air flow channel 643 via the second air flow channel 642.

Referring to both FIGS. 6A and 6B, the first layer 610, the second layer 620 and the third layer 630 each respectively has a first air flow channel 641, a second air flow channel 642 and a third air flow channel 643, and each air flow channel includes a plurality of sections that are not in communication with one another. The exhaust flow channel 650 is configured so that the sequence (1), the sequence (2) and the sequence (3) each flows through different sections of the first air flow channel 641. For example, when the sequence (1) flows through a section 641*a* of the first air flow channel 641, the subsequent sequence (2) flows through a section 641*b* of the first air flow channel 641, and the subsequent sequence (3) flows through a section 641*c* of the first air flow channel 641. Similarly, the exhaust flow channel 650 is configured so that the sequence (1), the sequence (2) and the sequence (3) each flows through different sections of the second air flow channel 642 from one another. For example, when the sequence (1) flows through a section 642*a* of the second air flow channel 642, the subsequent sequence (2) flows through a section 642*b* of the second air flow channel 642, and the subsequent sequence (3) flows through a section 642*c* of the second air flow channel 642. Similarly, the exhaust flow channel 650 is configured so that the sequence (1), the sequence (2) and the sequence (3) each flows through different sections of the third air flow channel 643 from one another. For example, when the sequence (1) flows through a section 643*a* of the third air flow channel 643, the subsequent sequence (2) flows through a section 643*b* of the third air flow channel 643, and the subsequent sequence (3) flows through a section 643*c* of the third air flow channel 643.

Seventh Embodiment

Figure 7:
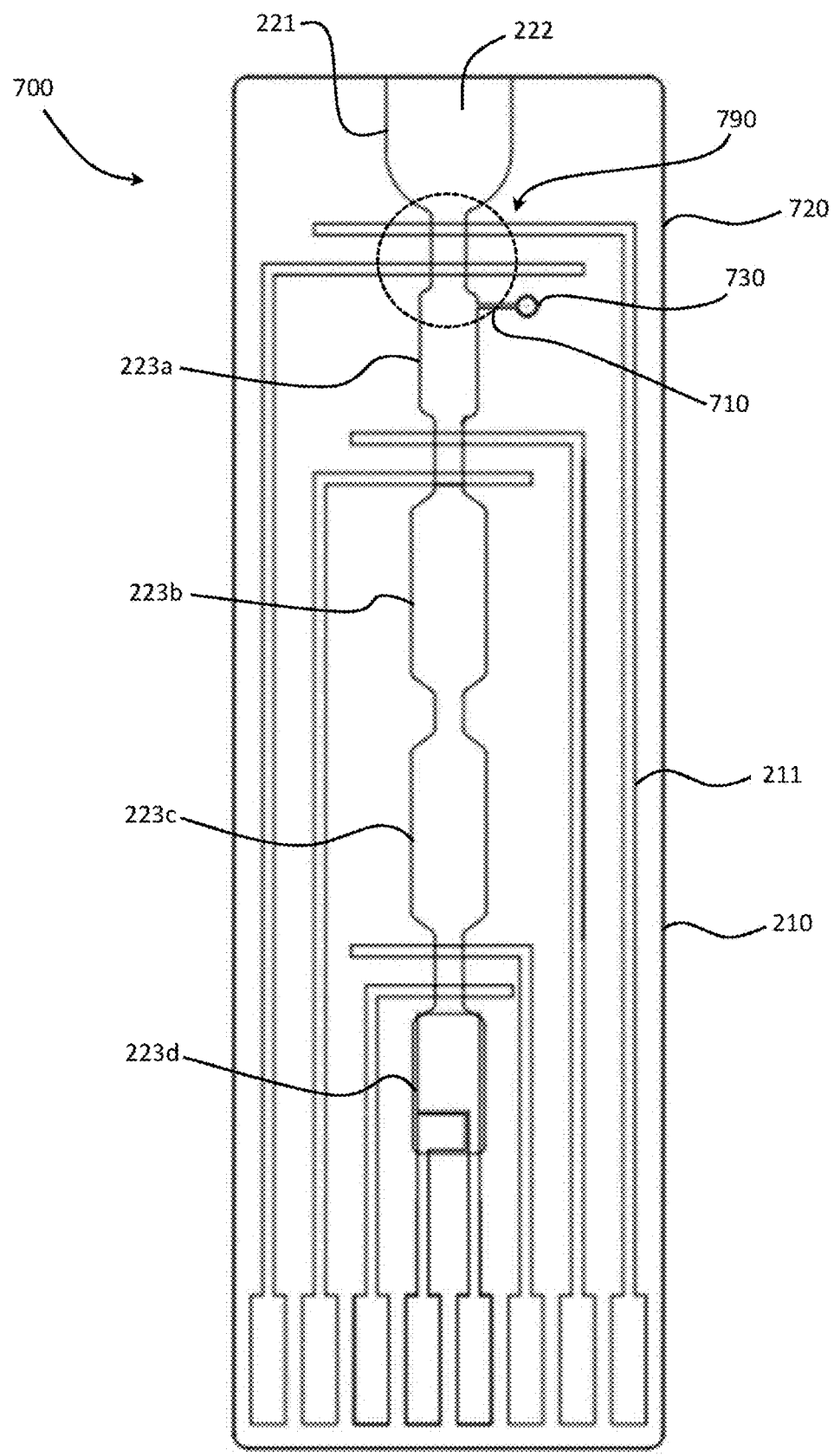
FIG. 7 is a schematic diagram of a biosensor strip according to a seventh embodiment of the present invention.

FIG. 7 shows a schematic diagram of a biosensor strip 700 of the seventh embodiment, and shows only a perspective diagram of a reaction layer 720 and the substrate layer 210 overlaid with each other. The biosensor strip 700 is similar to the biosensor strip 200 of the second embodiment, and differ in that the biosensor strip 700 further includes, at the reaction layer 720, a first auxiliary flow channel 710 and an auxiliary exhaust flow channel 730 capable of directly discharging into outside. The first auxiliary exhaust flow channel 710 is in communication with the reaction channel 221. In other embodiment, the auxiliary exhaust flow channel 730 can be located at another layer. The first auxiliary exhaust flow channel 710 is to allow the flow of the liquid sample in a first partial region of the reaction flow channel 221 faster than another region in the presence of the exhaust flow channel 241, wherein the first partial region includes an intersection of the reaction flow channel 221 and the first auxiliary exhaust flow channel 710. The first partial region can further include a sampling port 222 extending from the reaction flow channel 221 to the intersection of the reaction flow channel 221 and the first auxiliary exhaust flow channel 710, as a region 790 shown in FIG. 7. In this embodiment, the specific first partial region 710 in which the flow is to be accelerated is configured such that the liquid sample first comes into contact with the auxiliary exhaust hole 730 and then arrives at the through hole 250 corresponding to the exhaust flow channel 241. Referring to FIG. 7, in this embodiment, the first auxiliary exhaust flow channel 710 allows the liquid sample to enter therein. When the liquid sample enters the sampling port 222, the first auxiliary exhaust flow channel 710 determines the flow of the liquid sample, and when the first auxiliary exhaust flow channel 710 is with no air resistance function, the flow of the liquid sample is determined by the capillary action of the reaction flow channel 221. Then, when the liquid sample fills the first auxiliary flow channel 710, the function of the first auxiliary flow channel 710 becomes off (not in communication with the atmosphere). At this point, the flow of the liquid sample in the reaction flow channel 221 turns back to be controlled by the exhaust flow channel 241. The first auxiliary exhaust flow channel 710 is a channel between the reaction flow channel 221 and the auxiliary exhaust hole 730 for directly discharging into outside. The flow of the liquid sample in the reaction flow channel 221 is more accelerated as the first auxiliary exhaust flow channel 710 gets shorter. It should be noted that, in this embodiment, the first auxiliary exhaust flow channel 710 is in communication with the atmosphere when the liquid sample has not yet entered the sampling port 222, and such state thereof is referred to as an on state. In other embodiments, the first auxiliary exhaust flow channel 710 can be selectively disposed on any position of the reaction flow channel 221, for example, at one or more of the plurality of reagent areas. In light of the above, it should be understood that the first auxiliary exhaust flow channel 710 can replace the exhaust flow channel 241 to determine the flow of the liquid sample in the first partial region of the reaction flow channel 221.

In another embodiment, apart from the first auxiliary exhaust flow channel 710, the reaction layer 720 of the biosensor strip 700 further includes a second auxiliary exhaust flow channel (not shown). The second auxiliary exhaust flow channel is configured such that the liquid sample entering from the sampling port 22 first arrives at the first auxiliary exhaust flow channel 710, then arrives at the second auxiliary exhaust flow channel by passing one section of the exhaust flow channel 241, then further passing another section of the exhaust flow channel 241, and finally arrives at the through hole 250 corresponding to the exhaust flow channel 241. Different from the first auxiliary exhaust flow channel 710, the second auxiliary exhaust flow channel is in a off state (not in communication with the atmosphere) when liquid sample has not entered the first auxiliary exhaust flow channel yet. After the liquid sample closes the first auxiliary exhaust flow channel 710, the second auxiliary exhaust flow channel can be transformed from the off state to an on state (in communication with the atmosphere) at an appropriate timing, so as to accelerate the flow of the liquid sample in a second partial region of the reaction flow channel 241. Various appropriate methods can be used to transform the second auxiliary exhaust flow channel from the off state to the on state. For example, upon the electrode unit 211 detecting that the liquid sample flows through a specific position of the reaction flow channel 241, the second auxiliary exhaust flow channel is activated to become open (on). In this embodiment, when the liquid sample has not entered the sampling port 222, in the presence of the exhaust flow channel 241 (*on*), the first auxiliary exhaust flow channel 710 is on and the second auxiliary flow channel is off. When the liquid sample enters the sampling port 222 (entering the first partial region of the exhaust flow channel 241), the first auxiliary exhaust flow channel 710 determines the flow of the liquid sample. When the liquid sample fills the first auxiliary exhaust flow channel 710, the first auxiliary exhaust flow channel is off and the second auxiliary exhaust flow channel is not yet open (on), and the flow of the liquid sample at this point returns to the flow controlled by the exhaust flow channel 241. Then, the second auxiliary exhaust flow channel turns to be on, and the liquid sample enters a second partial region of the exhaust flow channel 241, and the second auxiliary exhaust flow channel at this point determines the flow of the liquid sample until the liquid sample fills the second auxiliary exhaust flow channel. When the liquid sample fills the first auxiliary exhaust flow channel 710 and also fills the second auxiliary exhaust flow channel, the flow of the liquid sample at this point returns to the flow controlled by the exhaust flow channel 241. In light of the above, it should be understood that the second auxiliary exhaust flow channel can replace the exhaust flow channel 241 to determine the flow of the liquid sample in the second partial region of the reaction of the reaction flow channel 221.

Eighth Embodiment

Figure 8:
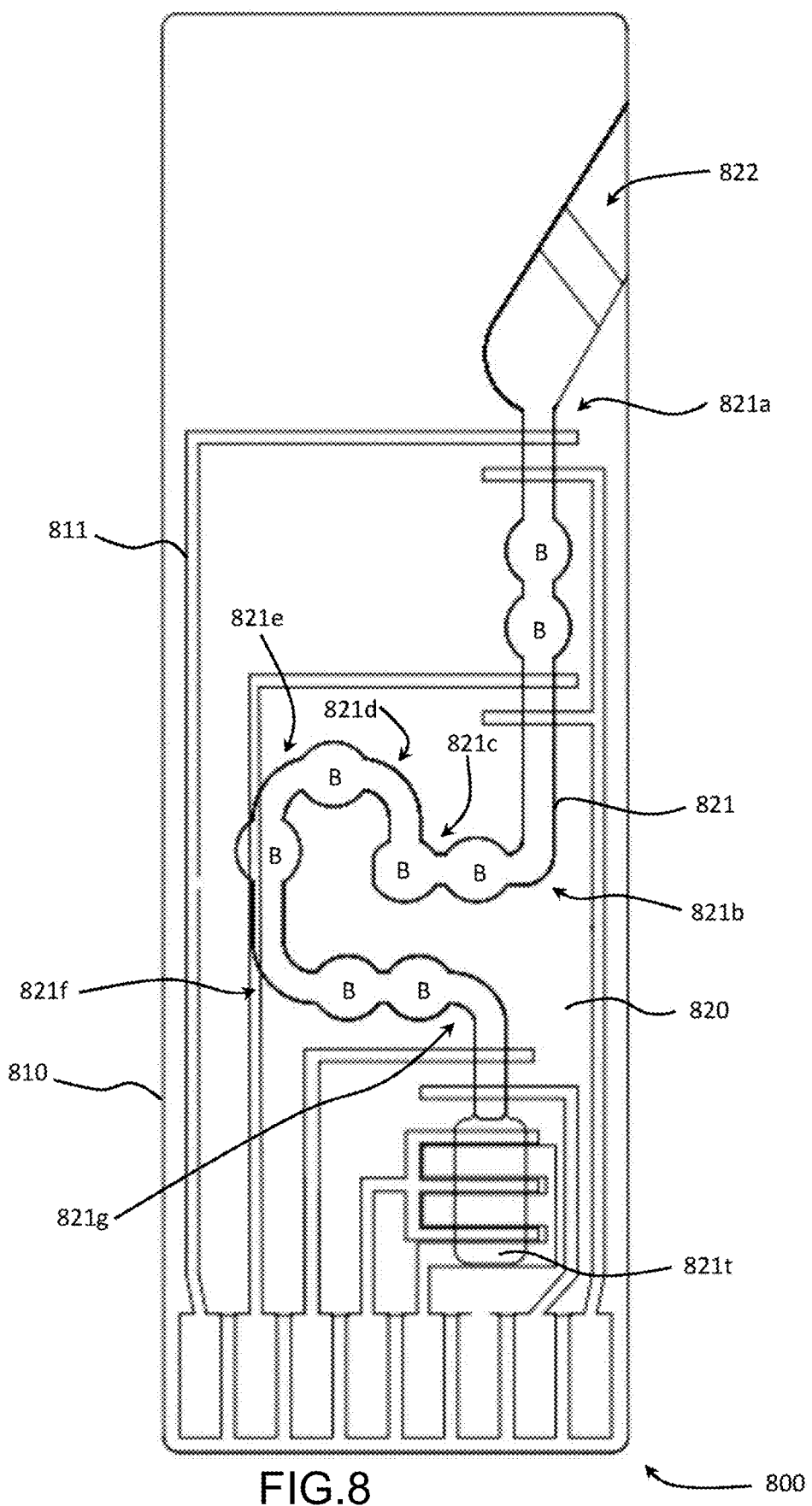
FIG. 8 is a schematic diagram of a biosensor strip according to an eighth embodiment of the present invention.

FIG. 8 shows a schematic diagram of a biosensor strip 800 of the eighth embodiment, and depicts a top-viewed perspective diagram of only a reaction layer 820 and a substrate layer 810 overlaid with each other. The biosensor strip 800 differs from the biosensor strip 200 of the second embodiment in respect of the configuration of a reaction flow channel 821 of the reaction layer 820 and the configuration of the electrode unit of the substrate layer 810. One feature of the eighth embodiment is that the path of the reaction flow channel 821 includes at least one bend, by which the flow of the liquid sample in the reaction flow channel 821 can be reduced. As shown, starting from a sampling port 822, the path of the reaction flow channel includes a bend 821a, a bend 821b, a bend 821c, a bend 821d, a bend 821e, a bend 821f and a bend 821g.

Referring to FIG. 8, another feature of the eighth embodiment is that the cross-section area of the reaction flow channel 821 changes with the different regions through which the reaction flow channel 821 flows. As shown, the cross-section area of the reaction flow channel 821 is not kept constant from the sampling port 822 to a terminal end 821t of the reaction flow channel 821, for example, regions B in the figure are all regions having greater cross-section areas. The flow of a specific first partial region of the reaction flow channel 821 can be fine-tuned by changing the cross-section area of the specific first partial region.

FIG. 9A, FIG. 9B and FIG. 9C show schematic diagrams of operating a conventional biosensor strip without an exhaust flow channel. The schematic diagram in FIG. 9A shows that a liquid sample S has just been dripped into a reaction flow channel 920 of a biosensor strip 900, and a timer T in FIG. 9A indicates that the time is 04 seconds. The schematic diagram in FIG. 9B shows that the liquid sample S has flown through more than ⅔ of the reaction flow channel 920, and a timer T in FIG. 9B indicates that the time is 06 seconds. The schematic diagram in FIG. 9C shows that the liquid sample S has arrived at the terminal end of the reaction flow channel 920, and a timer T in FIG. 9C indicates that the time is 07 seconds. It is demonstrated above that in the biosensor strip 900 without an exhaust flow channel, the time for the liquid sample S to fill the reaction flow channel is less than 10 seconds.

FIG. 10A, FIG. 10B, FIG. 100, FIG. 10D, FIG. 10E and FIG. 10F show schematic diagrams of operating a biosensor strip 1000 according to one embodiment of the present invention. The biosensor strip 1000 has an exhaust flow channel similar to that of the second embodiment. The shape of a reaction flow channel of the biosensor strip 1000 is the same as that of the biosensor strip 900. The schematic diagram in FIG. 10A shows that the liquid sample S has just been dripped into a reaction flow channel 1020 of the biosensor strip 1000, and a timer T in FIG. 10A indicates that the time is 31 seconds. FIG. 10B, FIG. 100, FIG. 10D, FIG. 10E and FIG. 10F sequentially show the process of the liquid sample S flowing through the reaction flow channel 1020 till the terminal end, wherein timers T in the respective schematic diagrams indicate that the time is 1 minute and 31 seconds, 2 minutes and 31 seconds, 3 minutes and 31 seconds, 4 minutes and 31 seconds, and 5 minutes and 44 seconds, respectively. It is demonstrated above that in the biosensor strip 1000 having an exhaust flow channel according to an embodiment of the present invention, the time for the liquid sample to fill the reaction flow channel 1020 is 5 minutes and 44 seconds.

Figure 11C:
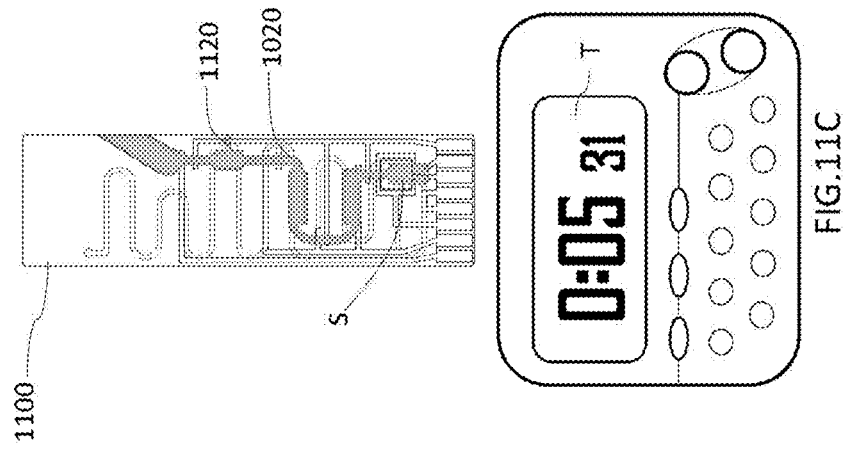
FIG. 11A, FIG. 11B and FIG. 11C are schematic diagrams of operating a biosensor strip according to an embodiment of the present invention.
Figure 11B:
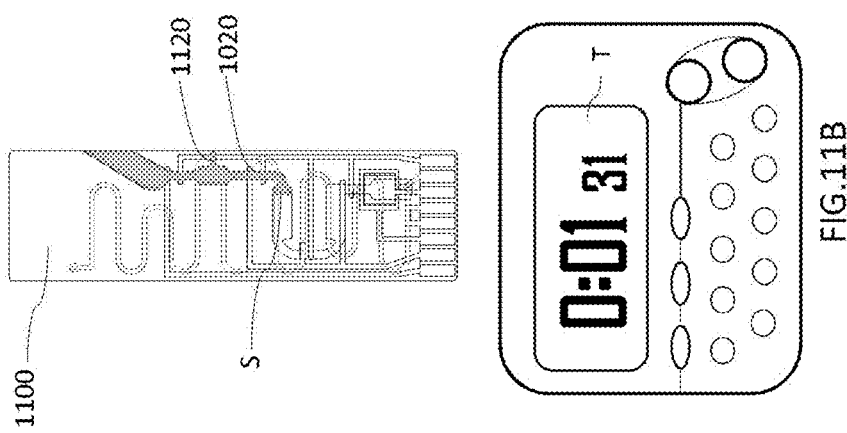
Figure 11A:
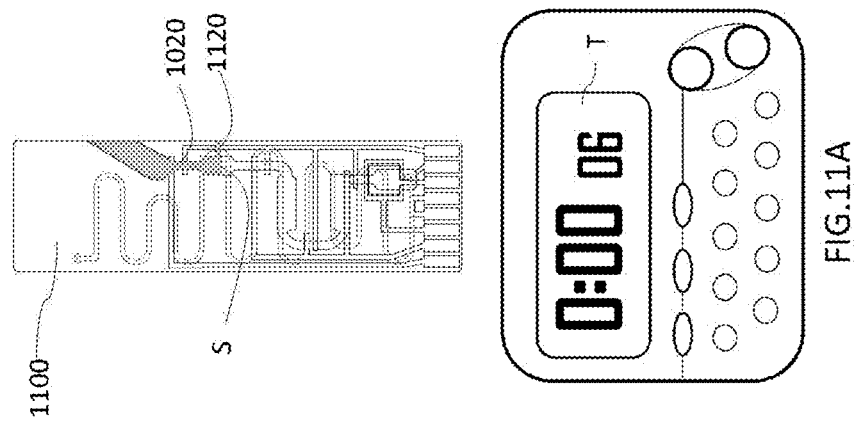

FIG. 11A, FIG. 11B and FIG. 11C show schematic diagrams of operating a biosensor strip 1100 according to an embodiment of the present invention. The biosensor strip 1100 has an exhaust flow channel similar to that of the second embodiment. The shape of a reaction flow channel of the biosensor strip 1100 is the same as that of the biosensor strip 1000; however, the biosensor strip 1100 additionally includes an auxiliary exhaust flow channel 1120. The schematic diagram in FIG. 11A shows that the liquid sample S has just been dripped into a reaction flow channel 1020 of the biosensor strip 1100 and rapidly fills the auxiliary exhaust flow channel 1120, and a timer T in FIG. 11A indicates that the time is 06 seconds. FIG. 11B and FIG. 11C sequentially show the process of the liquid sample S flowing through the reaction flow channel 1020 till the terminal end, and timers T in the respective schematic diagrams indicate that the time is 1 minute and 31 seconds and 5 minutes and 31 seconds, respectively. It is demonstrated above that in the biosensor strip 1100 having an exhaust flow channel and an auxiliary exhaust flow channel according to an embodiment of the present invention, the time for the liquid sample to fill the reaction flow channel is 5 minutes and 31 seconds, which is less than the time needed by the embodiment in FIG. 10A to FIG. 10F (having an exhaust flow channel but not an auxiliary exhaust flow channel).

Other specific forms can be used to embody the present invention without departing from the spirit or necessary features of the present invention, and the specific non-limiting embodiments in various aspects should be considered illustrative. Therefore, the scope of the present invention should be accorded with the appended claims but not as described in the foregoing description. All changes within equivalent meanings and ranges of the scope of the claims should be considered as within the scope of the claims.

SYMBOL DESCRIPTION f arrow/direction of air flow
V1 volume
V2 volume
100 biosensor strip
101 sampling end
110 substrate layer
120 reaction layer
121 reaction flow channel
130 separation layer
140 exhaust layer
141 exhaust flow channel
150 through hole
160 upper cover
161 exhaust hole
190 liquid sample
200 biosensor strip
201 sampling end
202 connecting end
210 substrate layer
211 electrode unit
220 reaction layer
221 reaction flow channel
221t terminal end
222 sampling port
223a, 223b, 223c, 223d reagent area
224 reagent
230 separation layer 231 first notch
241 exhaust flow channel
242 second notch
250 through hole
260 upper cover
261 exhaust hole
262 third notch
300 biosensor strip
310 hydrophilic layer
311 first exposure opening
312 second exposure opening
313 third exposure opening
410 choke valve
411 lower slot
412 middle slot
413 open
413p horizontal plane
414 bottom part
414c connecting part
415 upper slot
α wavefront arc
β contact angle
θ contact angle
w width
500 biosensor strip
510 first exhaust set
511 first layer
512 first upper cover
513 connecting hole
520 second exhaust set
521 second layer
522 second upper cover
523 exhaust hole
540 exhaust layer
541 first air flow channel
542 second air flow channel
550 exhaust flow channel
600 biosensor strip
610 first layer
620 second layer
630 third layer
640 exhaust layer
641 first air flow channel
641a, 641b, 641c sections
642 second air flow channel
642a, 642b, 642c sections
643 third air flow channel
643a, 643b, 643c sections
650 exhaust flow channel
660 upper cover
661 exhaust hole
700 biosensor strip
710 first auxiliary flow channel
720 reactive layer
730 auxiliary exhaust flow channel
790 region
800 biosensor strip
810 substrate layer
811 substrate layer
820 reactive layer
821 reaction flow channel
821a, 821b, 821c, 821d, 821e, 821f, 821g bend
B region
821t terminal end
821f bend
822 sampling port
900 biosensor strip
920 reaction flow channel
S liquid sample
T timer
1000 biosensor strip
1020 reaction flow channel
1100 biosensor strip
1120 auxiliary exhaust flow channel

The invention claimed is:

1. A biosensor strip, comprising:
a reaction layer, comprising a reaction flow channel;
a separation layer, located above the reaction layer and covering the reaction layer;
an exhaust layer, located above the separation layer, the exhaust layer comprising an exhaust flow channel and an exhaust hole configured to discharge air into outside and be in communication with the exhaust flow channel; and
a through hole, passing through the separation layer to communicate with the exhaust flow channel and the reaction flow channel;
wherein, the reaction flow channel comprises a sampling port, the reaction flow has a capillary structure configured to allow a liquid sample to enter the reaction flow channel through the sampling port, and the exhaust flow channel together with the exhaust hole are configured to reduce a flow of the liquid sample in the reaction flow channel provided by a capillary action; and
wherein, an air flow in the exhaust flow channel is configured to be smaller than the flow of the liquid sample provided by the capillary action.

2. The biosensor strip according to claim 1, wherein a resistance of air in the exhaust flow channel is $R_G$, a resistance difference between the liquid sample and air in the reaction flow channel is $\Delta R_L$, and $R_G \gg \Delta R_L$.

3. The biosensor strip according to claim 1, wherein the exhaust flow channel is distributed in a wave manner on the exhaust layer.

4. The biosensor strip according to claim 1, wherein the exhaust flow channel has a lateral cross section perpendicular to an extension direction of the exhaust flow channel, the lateral cross section has a long diameter and a short diameter, and a ratio of the long diameter to the short diameter is greater than 5.

5. The biosensor strip according to claim 1, wherein the through hole comprises a choke valve, the choke valve having a lower slot in communication with the reaction flow channel; and a middle slot located above the lower slot, wherein the lower slot has an opening in communication with the middle slot, the opening defining a horizontal plane, and the middle slot has a bottom part, the bottom part being formed with a connecting part to connect the opening, wherein a surface of the connecting part is not higher than the horizontal plane.

6. The biosensor strip according to claim 4, wherein the through hole comprises a hydrophobic inner wall.

7. The biosensor strip according to claim 1, wherein the exhaust layer comprises:
a first exhaust set, comprising a first air flow channel at a first layer, a first upper cover covering the first layer, and a connecting hole located at the first upper cover; and
a second exhaust set disposed above the first exhaust set, the second exhaust set comprising a second air flow channel at a second layer, a second upper cover covering the second layer, and an exhaust hole located at the second upper cover;

wherein, the first air flow channel, the connecting hole, the second air flow channel and the exhaust hole form the exhaust flow channel.

8. The biosensor strip according to claim 1, wherein the exhaust layer comprises a first layer, a second layer covering the first layer, and a third layer covering the second layer;
when a liquid sample enters the reaction flow channel, a flow direction of air in the exhaust flow channel comprises following sequences: (1) flowing from the first layer, passing through the second layer, and entering the third layer; (2) then flowing from the third layer, passing through the second layer, and returning to the first layer; and (3) again flowing from the first layer, passing through the second layer and entering the third layer.

9. The biosensor strip according to claim 1, the reaction layer comprising at least one auxiliary exhaust flow channel in communication with the reaction flow channel, wherein the auxiliary exhaust flow channel replace the exhaust flow channel to determine a flow of the liquid sample in a partial region of the reaction flow channel, and wherein the partial region further comprises an intersection of the reaction flow channel and the auxiliary exhaust flow channel.

10. The biosensor strip according to claim 9, wherein the partial region comprises a range from the sampling port of the reaction flow channel extended to the intersection of the reaction flow channel and the auxiliary exhaust flow channel.

* * * * *